(12) United States Patent
Tuysuzoglu et al.

(10) Patent No.: US 12,347,552 B2
(45) Date of Patent: Jul. 1, 2025

(54) MEDICAL DATA MANAGEMENT SYSTEM, METHOD AND COMPUTER PROGRAM

(71) Applicant: SIEMENS HEALTHINEERS AG, Forchheim (DE)

(72) Inventors: Ahmet Tuysuzoglu, Jersey City, NJ (US); Eli Gibson, Plainsboro, NJ (US); Dorin Comaniciu, Princeton, NJ (US)

(73) Assignee: Siemens Healthineers AG, Forchheim (DE)

( * ) Notice: Subject to any disclaimer, the term of this patent is extended or adjusted under 35 U.S.C. 154(b) by 356 days.

(21) Appl. No.: 17/446,635

(22) Filed: Sep. 1, 2021

(65) Prior Publication Data
US 2022/0101987 A1    Mar. 31, 2022

(30) Foreign Application Priority Data

Sep. 30, 2020  (DE) ................... 10 2020 212 398.5

(51) Int. Cl.
G16H 40/20  (2018.01)
G16H 10/60  (2018.01)
G16H 20/30  (2018.01)
G16H 30/00  (2018.01)

(52) U.S. Cl.
CPC ............. *G16H 40/20* (2018.01); *G16H 10/60* (2018.01); *G16H 20/30* (2018.01); *G16H 30/00* (2018.01)

(58) Field of Classification Search
CPC ................................................ G16H 40/20
See application file for complete search history.

(56) References Cited

U.S. PATENT DOCUMENTS

| | | | |
|---|---|---|---|
| 7,925,521 B2 | 4/2011 | Backhaus et al. | |
| 8,612,253 B2 | 12/2013 | Backhaus et al. | |
| 2006/0195339 A1* | 8/2006 | Backhaus | G16H 10/60 705/2 |
| 2009/0138318 A1 | 5/2009 | Hawkins et al. | |
| 2009/0196479 A1 | 8/2009 | Raman et al. | |
| 2010/0312581 A1* | 12/2010 | Wachtell | G16H 40/20 707/812 |
| 2013/0024382 A1* | 1/2013 | Dala | H04L 63/0464 705/51 |
| 2013/0132105 A1 | 5/2013 | Wood-salomon et al. | |
| 2013/0132142 A1 | 5/2013 | Wood-salomon et al. | |
| 2018/0018429 A1* | 1/2018 | Rice | G06F 16/248 |
| 2018/0315182 A1 | 11/2018 | Rapaka et al. | |

(Continued)

FOREIGN PATENT DOCUMENTS

WO    WO2020075172 A1    4/2020

OTHER PUBLICATIONS

Niculescu-Mizil, Alexandru, and Rich Caruana. "Predicting good probabilities with supervised learning." Proceedings of the 22nd international conference on Machine learning. 2005.

(Continued)

*Primary Examiner* — Van H Oberly

(57) ABSTRACT

A scheduling system includes: a plurality of input devices configured to output medical data, a workforce storage, configured to store working characteristics of a plurality of doctors, and a scheduler configured to receive as input data related to the medical data and the working characteristics, and configured to provide as output a plurality of schedules for the plurality of doctors for analysing the medical data.

17 Claims, 5 Drawing Sheets

(56) References Cited

U.S. PATENT DOCUMENTS

2020/0069973 A1     3/2020   Lou et al.
2020/0211695 A1     7/2020   Zheng et al.

OTHER PUBLICATIONS

Platt, John. "Probabilistic outputs for support vector machines and comparisons to regularized likelihood methods." Advances in large margin classifiers 10.3 (1999): 61-74.

* cited by examiner

MEDICAL DATA MANAGEMENT SYSTEM, METHOD AND COMPUTER PROGRAM

RELATED APPLICATION

This application claims the benefit of DE 10 2020 212 398.5, filed Sep. 30, 2020, which is hereby incorporated by reference in its entirety.

BACKGROUND

Timely interpretation of medical data, such as radiological images, in vitro data, patient monitored data, and consequent patient management is critical for achieving the best patient outcomes. Achieving this requires having the right data, such as imaging studies, interpreted by the right doctor, such as a radiologist, a pathologist, or a surgeon, at the right time.

This is challenging for a hospital, due to the continuous generation of medical data, the complexity of clinical information and hospital systems and the coordination required between many clinicians, imaging systems and hospital information systems.

Moreover, even for smaller hospitals, and more so for larger ones, the availability of the various doctors is variable, and their competences are variable as well, as some might specialize in different organs and/or medical conditions. It is challenging to ensure that the schedule according to which the various doctors process the incoming medical data is optimized.

Furthermore, the recent expansion of AI in medical data analysis, such as assisting in radiology, has led to the emergence of opportunities and new coordination challenges. Multiple automated systems have demonstrated improvements in interpretation times for specific imaging studies in isolation, by prioritizing studies with AI-detected critical findings. However, incorporating multiple such systems in a hospital system without coordinating their prioritization results in priority conflicts that may hurt global interpretation times.

The known systems operate so as to schedule the analysis of the medical data, either in its original form or after AI manipulation, by the doctors in simple manners, such as based on a first-in-first-out queue or based on a priority ranking. In the latter case, priority rankings usually are based on an input given by the requesting entity, such as the doctor in charge of the patient, the ER, or the ICU, and are thus subjective and might suffer from abuse, since the requesting entity usually has an incentive in getting its own medical data analysed first and/or cannot compare the urgency of its request to the global workload of the hospital.

SUMMARY AND DESCRIPTION

There is therefore a need to ensure that the schedule according to which the various doctors process the incoming medical data is optimized with respect to a plurality of parameters, such as the doctors' working hours, the association of a given medical condition to the best available doctor for its analysis, the urgency associated to each patient and the respective medical data, budgetary constraints, etc.

A dynamic scheduling system incorporating a scheduler can be used to optimize the scheduling for analysing medical data. This framework can incorporate multiple information sources, multiple constraints, and multiple objectives.

The system can dynamically create schedules for assigning the medical data to available doctors, so as to optimize the objectives while operating within the given constraints, based on an analysis of the medical data. The system can continuously optimize the scheduling based on the incoming medical data.

Moreover, aspects of the embodiments relate to methods which allow scores associated to the medical data to be equalized, or calibrated. That is, in order to avoid skewing the operation of the scheduler due to scores created in a non-unitary manner, for instance because they have been generated by different devices using different approaches to the score computation, the embodiments can provide techniques that allow such scores to be equalized among them.

An embodiment can relate to a scheduling system, including a plurality of input devices configured to output medical data, a workforce storage, configured to store working characteristics of a plurality of doctors, and a scheduler configured to receive as input data related to the medical data, and the working characteristics, and configured to provide as output a plurality of schedules for the plurality of doctors for analysing the medical data.

In some embodiments, the data related to the medical data can be the medical data.

In some embodiments, the scheduler can be configured so as to construct the plurality of schedules so as to maximize a correspondence between a medical condition associated to the medical data and specialties of the plurality of doctors and to minimize a turn-around-time for analysing the medical data in consideration of the urgency of the various conditions associated with the various pieces of medical data.

In some embodiments, the scheduling system can further include a plurality of data analysers, configured to receive the medical data from the plurality of input devices, analyse the medical data so as to assign a score indicative of urgency of the medical data and configured to output a scored medical data, and wherein the data related to the medical data can be the scored medical data.

In some embodiments, the scheduling system can further include a plurality of data analysers, configured to receive the medical data, analyse the medical data so as to assign a score indicative of urgency of the medical data, and output a scored medical data, and a score calibrator, configured to receive the scored medical data, analyse the scored medical data so as to calibrate the score of the medical data, and output a calibrated medical data, and wherein the data related to the medical data can be the calibrated medical data.

In some embodiments, the scored medical data can includes a plurality of pieces of scored medical data, any given piece of scored medical data including medical data and a risk score, wherein the score calibrator, for the act of analysing the scored medical data, can be configured to carry out a score calibration method including the acts of: for a given piece of scored medical data, estimating prior probability as empirical probabilities reported in literature or measured from historical records, for the given piece of scored medical data, estimating conditional probabilities for relevant findings as a function of the risk score associated to the given piece of scored medical data, constructing a graphical model of an interrelation between the plurality of risk scores and the plurality of findings, and inferring a posterior probability of a clinical state associated to the given piece of medical data, preferably using Bayesian inference.

In some embodiments, the score calibrator, for the act of estimating conditional probabilities, can be configured to estimate conditional probabilities using documented performance measures, preferably sensitivity and specificity, and/ or using classifier calibration techniques, preferably as isotonic regression and/or Platts scaling.

In some embodiments, the scheduling system can further include an objective storage configured to store one or more objectives for the operation of the scheduler, wherein the scheduler can further be configured to receive as input the one or more objectives.

In some embodiments, the scheduling system can further include a constraints storage configured to store one or more constraints, wherein the scheduler can further be configured to receive as input the one or more constraints.

In some embodiments, the medical data can include one or more of radiology image, in vitro data, and recorded patient data.

A further embodiment can relate to a scheduling method including the acts of: receiving as input data related to medical data output by a plurality of input devices, and working characteristics of a plurality of doctors, and providing as output a plurality of schedules for the plurality of doctors for analysing the medical data.

In some embodiments, the data related to the medical data can be the medical data.

In some embodiments, the scheduling method can further include an act of constructing the plurality of schedules so as to maximize a correspondence between a medical condition associated to the medical data and specialties of the plurality of doctors and minimize a turn-around-time for analysing the medical data in consideration of the urgency of the various conditions associated with the various pieces of medical data.

In some embodiments, the scheduling method can further include the acts of receiving the medical data from a plurality of input devices, analyse the medical data so as to assigning a score indicative of urgency of the medical data, and outputting a scored medical data, wherein the data related to the medical data can be the scored medical data.

In some embodiments, the scheduling method can further include the acts of receiving the medical data, analysing the medical data so as to assign a score indicative of urgency of the medical data, outputting a scored medical data, receiving the scored medical data, analysing the scored medical data so as to calibrate the score of the medical data, and outputting a calibrated medical data, and wherein the data related to the medical data can be the calibrated medical data.

In some embodiments, the scored medical data can include a plurality of pieces of scored medical data, any given piece of scored medical data including medical data and a risk score, wherein the act of analysing the scored medical data can include a score calibration method including the acts of: for a given piece of scored medical data, estimating prior probability as empirical probabilities reported in literature or measured from historical records, for the given piece of scored medical data, estimating conditional probabilities for relevant findings as a function of the risk score associated to the given piece of scored medical data, constructing a graphical model of an interrelation between the plurality of risk scores and the plurality of findings, and inferring a posterior probability of a clinical state associated to the given piece of medical data, preferably using Bayesian inference.

In some embodiments, the act of estimating conditional probabilities can include estimating conditional probabilities using documented performance measures, preferably sensitivity and specificity, and/or using classifier calibration techniques, preferably as isotonic regression and/or Platts scaling.

In some embodiments, the scheduling method can further include the acts of storing one or more objectives for the operation of the scheduler, receiving as input the one or more objectives.

In some embodiments, the scheduling method can further include the acts of storing one or more constraints, receiving as input the one or more constraints.

In some embodiments, the medical data can include any of radiology image, in vitro data, and recorded patient data.

Further embodiments of the embodiments can relate to a computer program or a computer-program product or a computer-readable storage medium including program code. The program code can be loaded and executed by at least one processor. Upon loading and executing the program code, the at least one processor can perform a scheduling method for processing of medical data in accordance with any of the methods described. It is to be understood that the features mentioned above and those yet to be explained below may be used not only in the respective combinations indicated, but also in other combinations or in isolation without departing from the scope of the invention.

DETAILED DESCRIPTION OF THE PREFERRED EMBODIMENTS

Figure 1:
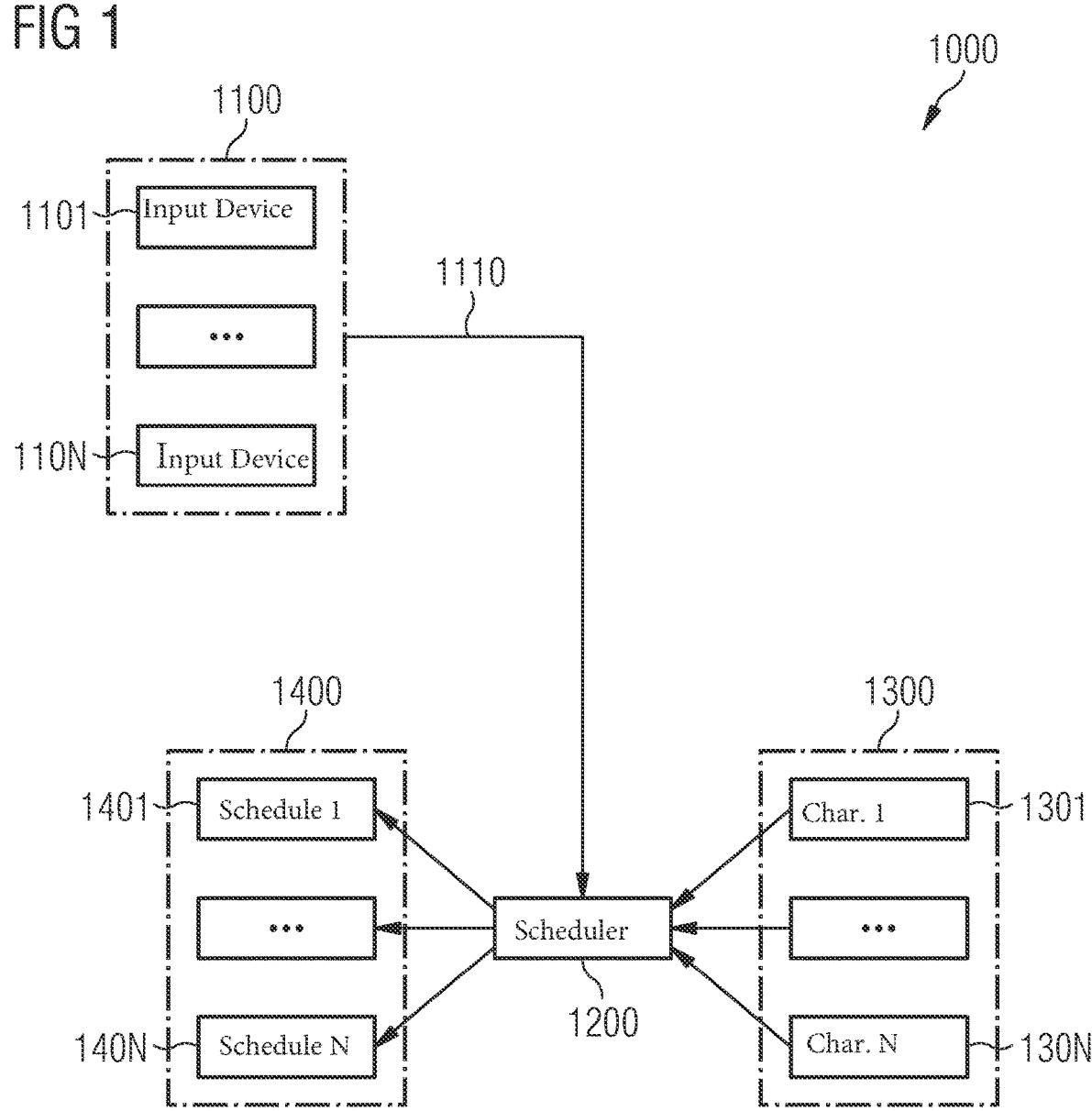
FIG. 1 schematically illustrates a scheduling system 1000 according to one embodiment.

Some examples of the present disclosure generally provide for a plurality of circuits or other electrical devices. All references to the circuits and other electrical devices and the functionality provided by each are not intended to be limited to encompassing only what is illustrated and described herein. While particular labels may be assigned to the various circuits or other electrical devices disclosed, such labels are not intended to limit the scope of operation for the circuits and the other electrical devices. Such circuits and other electrical devices may be combined with each other and/or separated in any manner based on the particular type of electrical implementation that is desired. It is recognized that any circuit or other electrical device disclosed herein may include any number of microcontrollers, a graphics processor unit (GPU), integrated circuits, memory devices (e.g., FLASH, random access memory (RAN), read only memory (ROM), electrically programmable read only memory (EPROM), electrically erasable programmable read only memory (EEPROM), or other suitable variants thereof), and software which co-act with one another to perform operation(s) disclosed herein. In addition, any one or more of the electrical devices may be configured to execute a program code that is embodied in a non-transitory computer readable medium programmed to perform any number of the functions as disclosed.

In the following, embodiments of the invention will be described in detail with reference to the accompanying drawings. It is to be understood that the following description of embodiments is not to be taken in a limiting sense. The scope of the invention is not intended to be limited by the embodiments described hereinafter or by the drawings, which are taken to be illustrative only.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

According to the techniques described herein, it is possible to obtain a plurality of pieces of medical data to be processed by a plurality of doctors and compute a plurality of schedules for the processing of those pieces of medical data based on various characteristics of the medical data as well as constraints associated to the doctors, such as their working hours.

According to various scenarios, it would be possible that such functionality is implemented in a hospital picture archiving and communications system, e.g., for radiological images implementing the imaging data. This is sometimes referred to as Picture archiving and communication system (PACS). Here, medical data acquired may be push notified to multiple subscribers.

In the context of this application, the term medical data is understood to generally relate to medically relevant data for enabling a diagnosis of a patient. In particular, the medical data can include one or more among a radiology image, in vitro data, and recorded patient data, such as any of temperature, blood pressure, weight, height, age, medical history, clinical score, etc.

The medical data does not need to have a specific format and can, for instance, include a combination of images and text, such as a magnetic resonance image and the patient's medical history.

In some cases, as it will appear more clearly from the subsequent description, the medical data can include one or more tags, which might be added to, or modified, during processing of the medical data. The tag can include information such as a numerical measurement of gravity or urgency of the medical data as judged by a requesting entity or by an artificial intelligence analysis of the medical data.

FIG. 1 schematically illustrates a scheduling system 1000 including a plurality of input devices 1100, 1101-110N configured to output medical data 1110.

The input devices 1100, 1101-110N can include any device capable of outputting medical data 1110 which can be used for the diagnosis of a patient, and in particular any of:
  medical imaging devices, such as X-ray imaging, magnetic resonance imaging, ultrasound imaging, echocardiogram, etc.
  medical measuring devices, such as a thermometer, an electrocardiogram machine, an oxygen saturation monitor, a sphygmomanometer, etc., or
  computing devices, such as a personal computer, a tablet, or a smartphone, which can be used by medical personnel to collect medical data manually, for instance based on an interview. This could apply, for instance, to the age and weight of the patient but also to description of pain locations and levels, or more general to a description of symptoms, etc.

The scheduling system 1000 can further include a workforce storage 1300, configured to store working characteristics 1301-130N of a plurality of doctors. The workforce storage, as well as other storages described throughout the application, can be implemented by any storage device, such as a hard-disk or a memory, and can store the working characteristics 1301-130N as digital data. The working characteristics 1301-130N can include, for each of a plurality of doctors, any of:
  working availability of doctors, such as a combination of days and hours at which those doctors are expected to be working,
  specialties of the doctors, such as an indication of a medical field, for instance by an alphanumeric string identifying the fields such as "cardiology", "neurology", "ophthalmology", etc.
  turnaround time for evaluating medical data based on statistics from previous analysis etc.

For instance, the following can illustrate a schematic content of an exemplary workforce storage 1300 storing working characteristics 1301-1303 of three doctors:

|  | Doctor X | Doctor Y | Doctor Z |
| --- | --- | --- | --- |
| Working availability | Mon-Fri 9.00-17.00 | Mon-Fri 12.00-20.00 | Mon-Wed 10.00-16.00, Fri 10.00-16.00, |
| Specialty | Cardiology | General Radiology | Neurology |
| Turn-around-time | 2 H 23 min | 0 h 45 min | 1 h 25 min |

The scheduling system 1000 can further include a scheduler 1200 configured to receive as input data related to the medical data 1110 and the working characteristics 1301-130N. In the implementation illustrated in FIG. 1, the data related to the medical data 1110 is the medical data 1110 itself.

The scheduler 1200, as well as other schedulers described throughout the application, can be implemented, in some embodiments, as a computing device implementing optimization methods that are instances of mixed integer linear programming and/or mixed integer non-linear programming. These methods enable the scheduler 1200 to mathematically express constraints and objectives which will be described later.

Alternatively, or in addition, in some embodiments the scheduler 1200, as well as other schedulers described throughout the application, can be implemented as a neural network.

The scheduler 1200 can be configured to provide as output a plurality of schedules 1401-140N for the plurality of doctors for analysing the medical data 1110. In some embodiments, the schedules can be a combination of at least an identifier of a piece of medical data, for instance an X-ray image, and a schedule for a given doctor for analysing the piece of medical data identified by the identifier.

For instance, in some cases, the schedules could be implemented as a list of identifiers of pieces of data for a given doctor. For instance, the following can illustrate a schematic illustration of the schedules 1401-140N for the three doctors X, Y, Z of the previous examples, assuming ten pieces of medical data D1-D10 to be analysed:

| Doctor X | Doctor Y | Doctor Z |
|----------|----------|----------|
| D1       | D10      | D6       |
| D5       | D9       | D7       |
|          | D4       |          |
|          | D8       |          |
|          | D3       |          |
|          | D2       |          |

That is, the schedules might include one or more schedules, each schedule being associated to one doctor, for instance through an appropriate identifier, where the schedule of a given doctor includes at least an ordered list of pieces of medical data to be analysed, preferably ordered based on their urgency.

In some embodiments, the schedule of a given doctor can further include time information, preferably associated to the piece of medical data, so as to also inform the doctor about the time at which the analysis of the piece of medical data is expected. An example of this approach is schematically illustrated in the following:

|                 | Doctor X | Doctor Y | Doctor Z |
|-----------------|----------|----------|----------|
| Mon 9.00-10.00  | D1       | D10      |          |
| Mon 10.00-11.00 |          | D9       | D6       |
| Mon 11.00-12.00 |          | D4       |          |
| Mon 12.00-13.00 | D5       | D8       | D7       |
| Mon 13.00-14.00 |          | D3       |          |
| Mon 14.00-15.00 |          | D2       |          |

In some embodiments, the schedules outputted by the scheduling system can be integrated into radiology information systems (technical devices coordinating the image readings) or hospital information systems so that the objectives are realized.

In some embodiments, the scheduler 1200 can be configured so as to construct the plurality of schedules 1401-140N so as to
maximize a correspondence between a medical condition associated to the medical data 1110 and the specialties of the plurality of doctors, and so as to minimize a turn-around-time for analysing the medical data 1110.

In particular, in some embodiments, the turn-around-time can be minimized as a function of the urgency of the various conditions associated with the various pieces of medical data, with the more urgent medical conditions being scheduled to receive a lower turn-around-time and the less urgent medical conditions being scheduled to receive a higher turn-around-time.

In the example above, for instance, it can be considered that D2 had less urgency than D10, for instance because of a more urgent medical condition, such as a haemorrhage vs. a fracture. Still for instance, in the example above, of it can be considered that D5, which is scheduled to be analysed at the same time as D7, was related to a medical condition more related to cardiology than to neurology and thus associated to a doctor more expert in cardiology, and vice versa.

Figure 2:
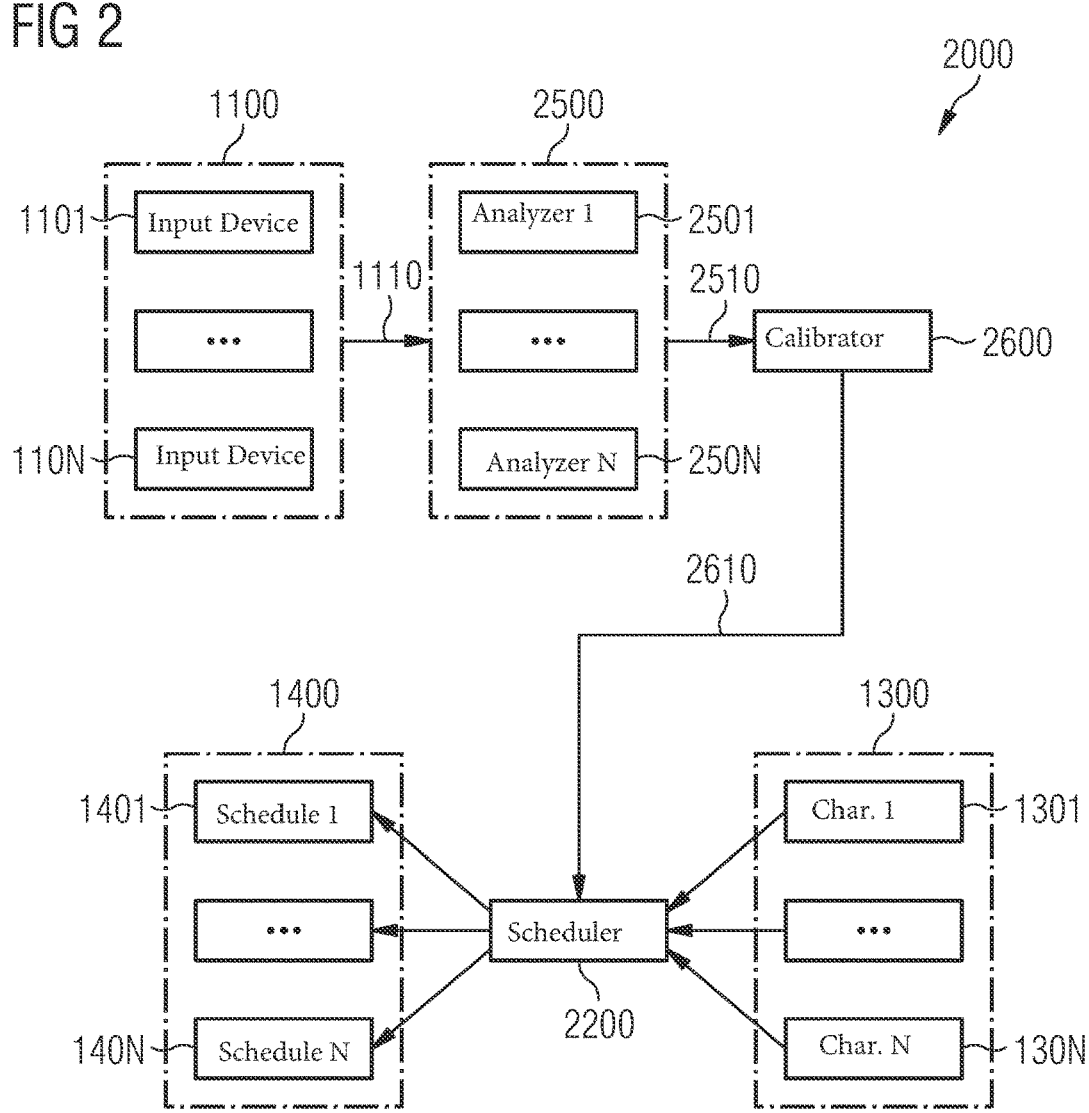
FIG. 2 schematically illustrates a scheduling system 2000 according to another embodiment.

FIG. 2 schematically illustrates a scheduling system 2000. The scheduling system 2000 differs from scheduling system 1000 by further including a plurality of data analysers 2500, 2501-250N, configured to receive the medical data 1110 from the plurality of input devices 1100, 1101-110N, analyse the medical data 1110 so as to assign a score indicative of urgency of the medical data 1110, and output a scored medical data 2510.

The data analysers 2500 can include any of a manual, rule-based or neural network-based systems for judging the risk, or urgency, or priority, of the medical data.

In the manual mode, the risk can be for instance inserted by an operator, such as the entity requiring the analysis or by an operator performing a first level triage on the medical data 1110. In the rule-based and neural network-based mode, the risk can be associated to the medical data based on a set of predetermined rules and/or based on a neural network trained so as to associate a higher risk to more urgent conditions associated to the various pieces of medical data.

In some embodiments, the scheduling system 2000 differs from scheduling system 1000 in that it includes a scheduler 2200, which differs from scheduler 1200 in that the data related to the medical data provided as input to the scheduler 2200 is the scored medical data 2510.

In those embodiments, the scheduler 2200 can construct the plurality of schedules 1401-140N as previously described while also taking into account the level of urgency associated to the various pieces of medical data, in particular so as to reduce the turn-around-time as the urgency increases. In this manner, in addition to the advantages already obtained by the system 1000, it can also be ensured that more urgent pieces of medical data are analysed in a prioritized manner.

As still represented in FIG. 2, in some embodiments the system 2000 can further include a score calibrator 2600, configured to receive the scored medical data 2510, analyse the scored medical data 2510 so as to calibrate the score of the medical data 1110, and output a calibrated medical data 2610.

In particular, in cases in which the various data analysers 2501-250N operate independently of each other, there might be a problem in that the urgency scores given by the individual data analyser might be in relation to each other, while the urgency scores given by different individual data analysers might not. For instance, a given data analyser, i.e., data analyser 2101, might correctly determine that a piece of medical data 1110 has an urgency higher than another piece of medical data, correctly associating a 9/10 urgency score to the first piece of medical data and a 6/10 urgency score to the second piece of medical data. Similarly, another data analyser, i.e., data analyser 250N, might associate an urgency score of 8/10 to a third piece of medical data and 5/10 to a fourth piece of medical data. Due to the possibly different operation of the two data analysers, it might however be the case that the urgency scores from different data analysers are not directly comparable to each other. I.e., the 9/10 of the data analyser 2501 might actually be less urgent than the 8/10 of the data analyser 250N.

The score calibrator 2600 is intended to solve this potential issue. In particular, in some embodiments, the score calibrator 2600 can calibrate individual risk scores based on historical or contemporary empirical performance, performance models and/or prevalence at the healthcare system, hospital, departmental or scanner level.

The calibrated risk score can be combined into a common representation, such as a risk vector, to reflect the probability of each of a set of radiological findings or clinical states. More details on possible implementations of such risk vector will be provided in the description below.

Additionally, risk scores from some data sources, such as electronic health records (laboratory values, vital signs, and clinical history), may indicate a need for prioritization beyond the presence of specific findings. These calibrations can be done in advance or updated dynamically based on contemporary data.

Figure 3:
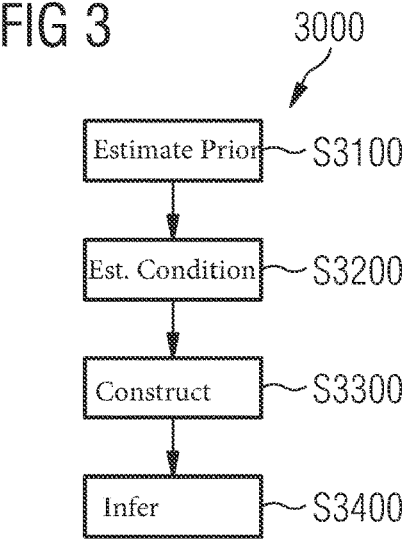
FIG. 3 schematically illustrates a score calibration method 3000 of one embodiment.

In particular, FIG. 3 schematically illustrates a score calibration method 3000 which can be carried out by the score calibrator 2600 for calibrating the scored medical data 2510. The score calibrator can be implemented as hardware or software.

Here, it is assumed that the scored medical data 2510 includes a plurality of pieces of scored medical data 2510, any given piece of scored medical data 2510 including medical data and a risk score, associated to the medical data.

The score calibrator 2600, for the act of analysing the scored medical data 2510, can thus be configured, for a given piece of scored medical data 2510, to carry out an act S3100 of estimating prior probability as empirical probabilities reported in literature or measured from historical records.

Furthermore, the score calibrator 2600 can be further configured, for the given piece of scored medical data 2510, to carry out an act S3200 of estimating conditional probabilities for relevant findings, as a function of the risk score associated to the given piece of scored medical data 2510.

In particular, in some embodiments, for the act S3200, of estimating conditional probabilities, the score calibrator 2600 can be configured to estimate S3200 the conditional probabilities using documented performance measures, preferably sensitivity and specificity, and/or using classifier calibration techniques, preferably as isotonic regression and/or Platts scaling.

Additionally, the score calibrator 2600 can be further configured to carry out an act S3300 of constructing a graphical model of an interrelation between the plurality of risk scores and the plurality of findings.

Those skilled in the art will recognize that the graphical model can be implemented in any manner allowing representation of conditional dependence between variables, such as the prior probabilities and the conditional probabilities described above, as a graph.

Moreover, the score calibrator 2600 can be further configured to carry out an act of S3400 inferring a posterior probability of a clinical state associated to the given piece of medical data, preferably using Bayesian inference.

In some embodiments, the posterior probabilities of the clinical states can then be used as weighting factors for the risk vector.

A simplified example of such an approach is provided in the following. It will be understood that the specific example is not intended to be limiting the invention but rather clarify the description.

A hospital system can have 3 AI systems:
one that detects haemorrhage,
one that detects haemorrhage and infarct, and
one that detects calvarial fractures.
In this exemplary implementation, various variables can be defined by table 1 and table 2 below.

TABLE 1

| Variable | Meaning | Values |
| --- | --- | --- |
| H | Patient has haemorrhage | Y/N |
| I | Patient has infarct | Y/N |
| F | Patient has fracture | Y/N |
| A | Primary reason for admission | Trauma, Stroke, Headache, etc. |
| N | Outcome of clinical evaluation for stroke | 0, 1, . . . , 42 |
| AI_1H | Score of AI1 for haemorrhage | 0-1 or n/a |
| AI_2H | Score of AI2 for haemorrhage | 0-1 or n/a |

TABLE 1-continued

| Variable | Meaning | Values |
| --- | --- | --- |
| AI_1I | Score of AI1 for infarct | 0-1 or n/a |
| AI_3F | Score of AI3 for fracture | 0-1 or n/a |

TABLE 2

| Dependence | Representation | Estimation |
| --- | --- | --- |
| P(H) | Conditional probability table | hospital historical records |
| P(I) | Conditional probability table | hospital historical records |
| P(F) | Conditional probability table | hospital historical records |
| P(A\|H, I, F) | Conditional probability table | hospital historical records |
| P(N\|I) | Parametric distribution | hospital historical records |
| P(AI_1H\|H) | Parametric distribution | literature or internal study |
| P(AI_2H\|H) | Parametric distribution | literature or internal study |
| P(AI_1I\|I) | Parametric distribution | literature or internal study |
| P(AI_3F\|F) | Parametric distribution | literature or internal study |

The conditional distributions in Table 2 can be fit to historical data or fit to contemporary data by recording the underlying disease states, clinical score, and AI scores in an internal study, and fitting the parametric models using expectation maximization. Notably, the conditional distribution of the AI score on the underlying disease state, for instance P(AI_1H|H) can be computed using the same data that is typically used for ROC analysis of AI classifiers.

A graphical model can be built containing the variables in Table 1 and the dependencies in Table 2, as schematically indicated below, where "=>" indicates a connection from a node to another in the graphical model:
$I \Rightarrow N$, $I \Rightarrow AI_{1,I}$, $I \Rightarrow A$;
$H \Rightarrow AI_{1,H}$, $H \Rightarrow AI_{2,H}$, $H \Rightarrow A$;
$F \Rightarrow A$, $F \Rightarrow AI_{3,F}$.

A calibrated risk score can thus be formulated as a vector of the posterior probabilities of I, H and F, given the observed medical data for the patient a, n, $a_{1,I}$, $ai_{1H}$, $ai_{2H}$, $ai_{3F}$:

$P\ I,H,F|A=a,N=n,AI_{1I}=a_{1I},AI_{1H}=ai_{1H},AI_{2H}=ai_{2H},$
$AI_{3F}=ai_{3F})$ $=P(I,H,F,A=a,N=n,AI_{1I}=ai_{1I},AI_{1H}=ai_{1H},AI_{2H}=ai_{2H},$
$AI_{3F}=ai_{3F})/P(A=a,N=n,AI_{1I}=ai_{1I},AI_{1H}=ai_{1H},$
$AI_{2H}=ai_{2H},AI_{HF}=ai_{3F})$ $=P(I)P(H)P(F)P(N=n|I)P(A=a|I,H,F)P$
$(AI_{1H}=ai_{1H}|H)P(AI_{2H}=ai_{2H}H)P(AI_{2I}=ai_{2I}|I)P$
$(AI_{3F}=ai_{2F}|F)/Sum\_\{I,H,F\}P(I,H,F,A=a,N=n,$
$AI_{1I}=ai_{1I},AI_{1H}=ai_{1H},AI_{2H}=ai_{2H},AI_{3F}=ai_{3F})$

This vector can then be used by the scheduler, as will result from the following description.

In the presence of the score calibrator 2600, the scheduling system 2000 thus differs from scheduling system 1000 in that it includes a scheduler 2200, which differs from scheduler 1200 in that the data related to the medical data provided as input to the scheduler 2200 the calibrated medical data 2610.

In those embodiments, the scheduler 2200 can thus construct the plurality of schedules 1401-140N as previously described while also ensuring that the various urgency scores associated to the various pieces of medical data are interpreted in a correct manner, even when outputted by a plurality of different data analysers 2501-250N.

Figure 4:
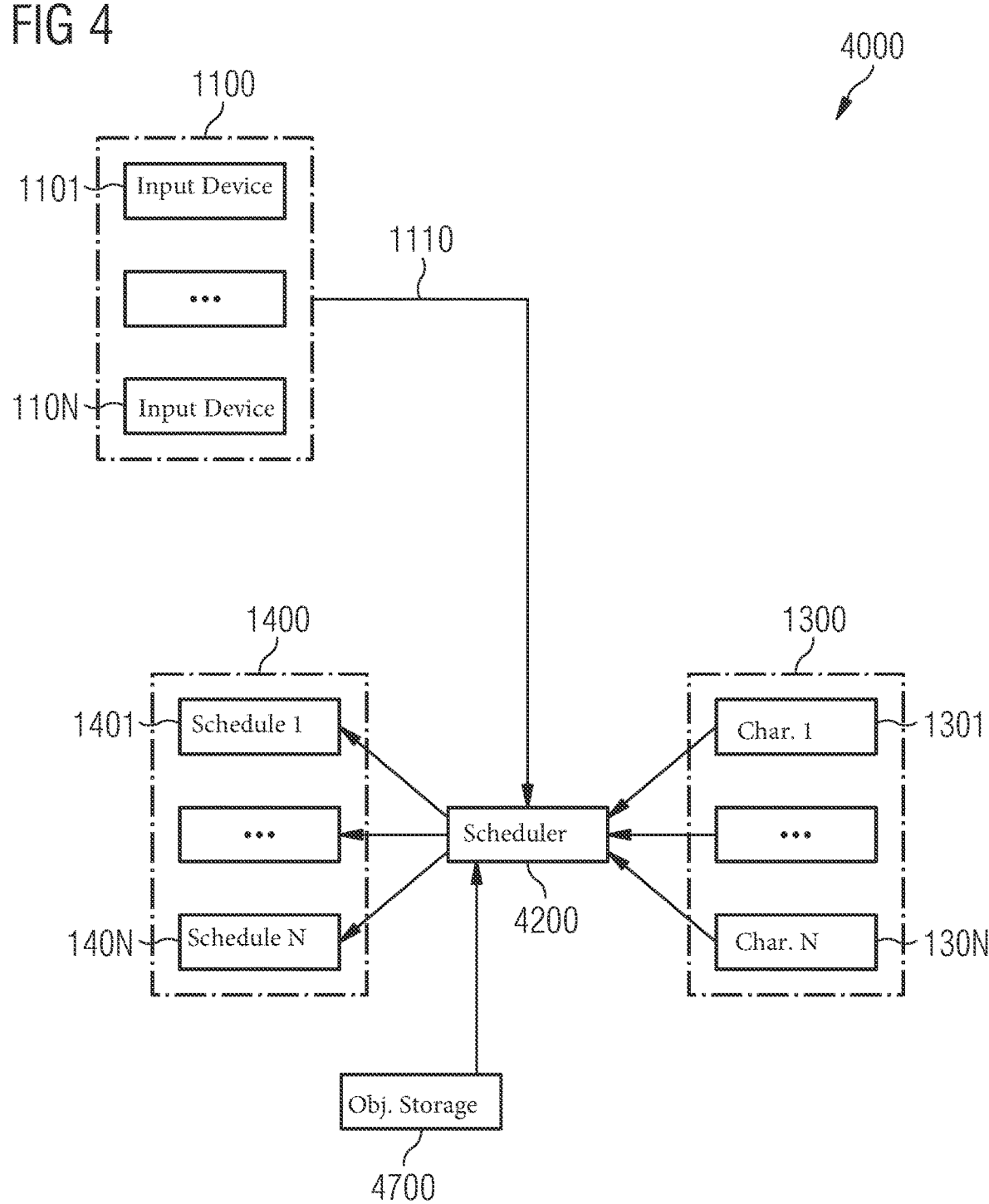
FIG. 4 schematically illustrates a scheduling system 4000 according to yet another embodiment.

FIG. 4 schematically illustrates a scheduling system 4000. The scheduling system 4000 differs from scheduling system 1000 by further including an objective storage 4700 configured to store one or more objectives for the operation of the scheduler 4200.

In particular, the objectives can be given as input to the scheduler 4200 so as to indicate to the scheduler 4200 what priorities are to be considered when constructing the schedules 1401-140N.

In the examples above some objectives have already been indicated, such as maximize a correspondence between a medical condition associated to the medical data 1110 and the specialties of the plurality of doctors and minimize a turn-around-time for analysing the medical data 1110.

In the previously described embodiments, those objectives might be stored in the scheduler, for instance at the configuration or during the training thereof. The presence of the objective storage 4700 allows the objectives for the scheduler 4200 to be controlled during the operation of the scheduler 4200, for instance by adding or removing objectives, or by changing the relative weight associated to the various objectives, which are then provided as an input to the scheduler 4200.

Each of objectives might include, for instance, a numerically expressed weight associated to a natural-language expressed goal, the goals including, for instance:
  maximize a correspondence between a medical condition associated to the medical data 1110 and the specialties of the plurality of doctors, this allows to achieve a higher analysis quality and reduce analysis time,
  minimize a turn-around-time for analysing the medical data 1110, this allows to generally obtain a speedy processing of the medical data,
  optimize a turn-around-time for analysing the medical data 1110 based on the risk score associated to it, the higher the risk score the lower the turn-around-time,
  balance analysing load among the various doctors, so that workload is evenly distributed to reduce burnout and maintain quality of service,
  minimize overtime, this allows to reduce burnout and increase the quality of the analysis,
  minimize operational cost, this allows to ensure financial viability of the hospital, for instance by, when two available doctors can both be assigned to a task, choosing the doctor with a lower cost, etc.

Figure 5:
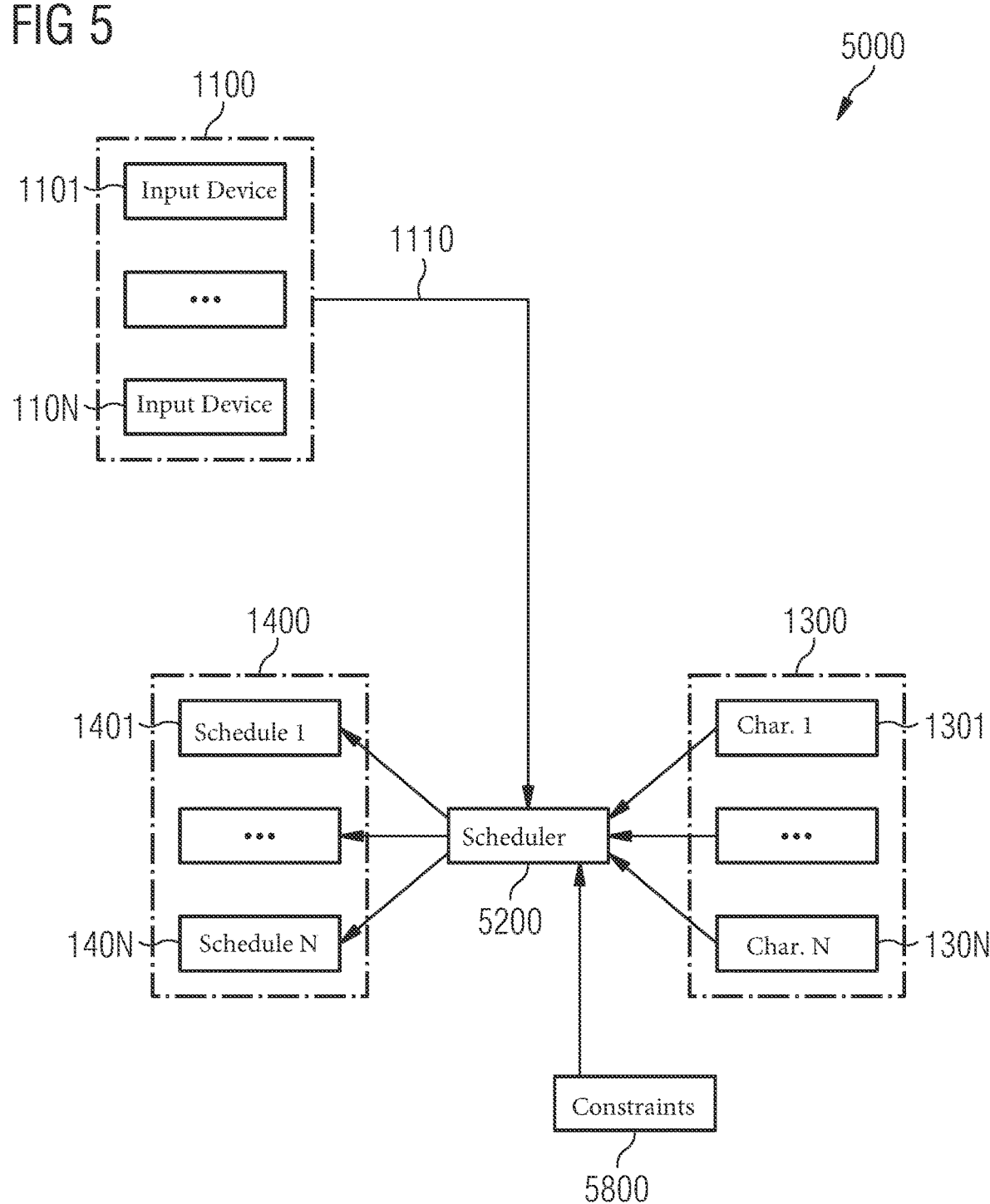
FIG. 5 schematically illustrates a scheduling system 5000 according to still another embodiment.

FIG. 5 schematically illustrates a scheduling system 5000. The scheduling system 5000 differs from scheduling system 1000 by further including a constraints storage 5800 configured to store one or more constraints 1301-130N. In some embodiments, as it will be clearer from the following description, the constraints might be doctor specific, that is, some constraints might have different values or different formulations depending on the specific doctor which is considered for the scheduling.

In particular, the constraints can be given as input to the scheduler 5200 so as to indicate to the scheduler 5200 what limits are to be considered when constructing the schedules 1401-140N.

Figure 6:
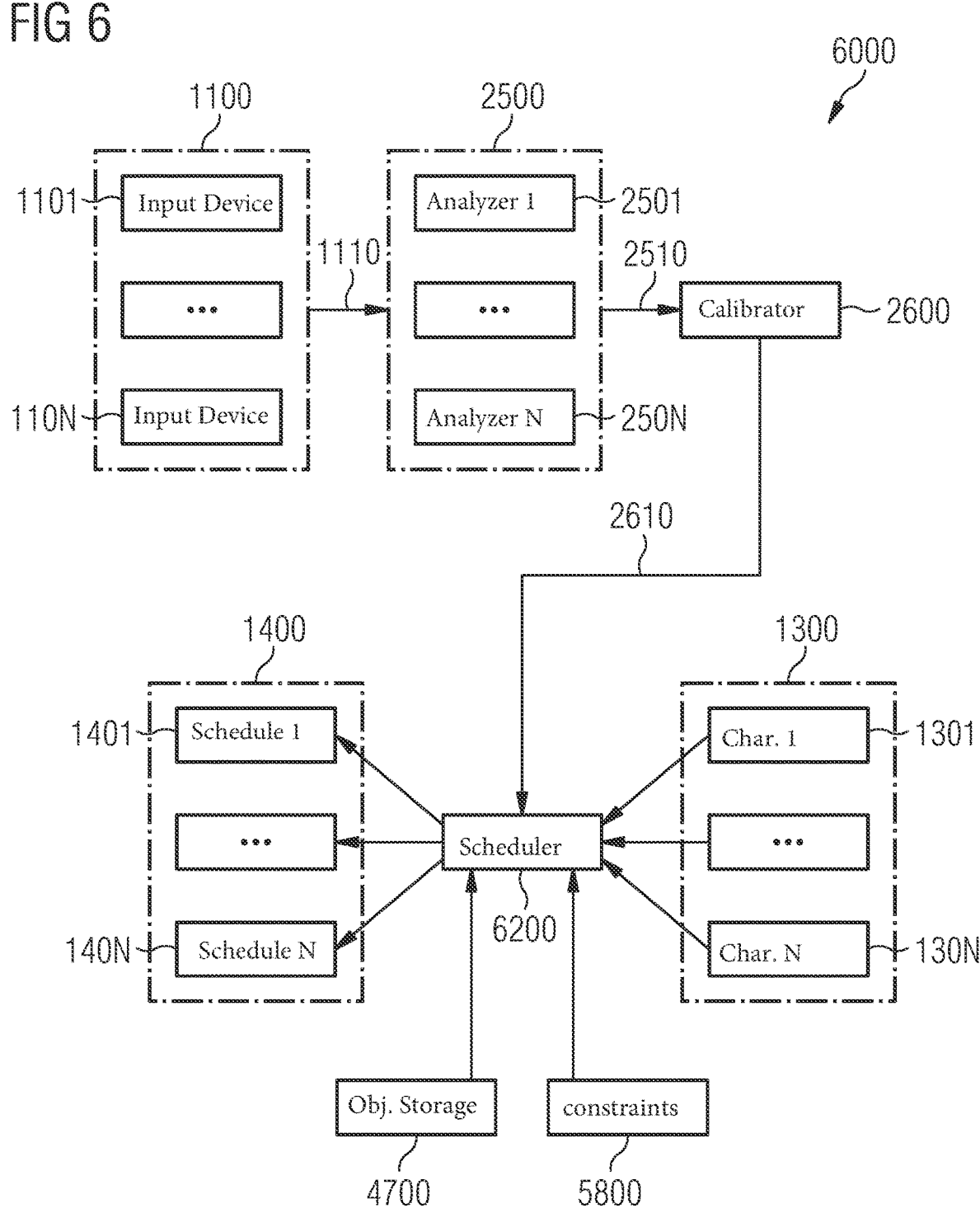
FIG. 6 schematically illustrates a scheduling system 6000 for another embodiment.

Each of the constraints might include, for instance, a numerically expressed weight associated to a natural-language expressed goal, the goals including, for instance:
  maximum interpretation time allowed for any piece of medical data 1100,
  maximum interpretation time as a function of the urgency, such as the risk score, or the medical data,
  maximum working hours of a given doctor, expressed daily and/or over a period of a plurality of days FIG. 6 schematically illustrates a scheduling system 6000. The scheduling system 6000 is an example of how the various features previously described with reference to scheduling systems 1000-5000 can be combined together. It will be clear to those skilled in the art that any combination of any of the features of the various scheduling systems described above can be implemented, and not only the exemplary combination illustrated in FIG. 5.

As it is clear from the description above, the embodiment therefore allows an optimization-based approach to be implemented for a scheduling system. In the following additional embodiments and specific implementation approaches are disclosed, which can be combined with the embodiments above.

Reading tasks, such as the pieces of medical data, are to be completed and a number of medical providers, such as doctors, can assess, evaluate, and complete the tasks. The task pool is assumed to be dynamic, such that new tasks can be added, and tasks can be removed as they are completed or taken off the pool for any reason.

In some embodiments, $x_{ijk}$ can denote a binary decision variable which indicates the assignment of task $i \in \mathcal{T}$ to medical provider $j \in \mathcal{P}$ at time unit $k \in \mathcal{K}$ where $\mathcal{T}$ and can $\mathcal{P}$ represent the sets of tasks and medical providers and $\mathcal{K} = \{1, 2, 3, \ldots, k_{max}\}$ can represent the ordered planning timeline with respect to time bins. It is then possible to define the following assignment variable:

$$x_{ijk} = \begin{cases} 1 & \text{if task } i \text{ is assigned to medical provider } j \text{ at time unit } k. \\ 0, & \text{otherwise.} \end{cases}$$

Each time bin can span a finite amount time and tasks can span more than a unit of these time slots. The duration of task i in terms of time units can be denoted as $d_i$.

Each task in the pool can be associated with an accumulated wait time, denoted by $w_i$, before the scheduling operation is executed. A binary variable can be defined to indicate the start time of the task:

$$y_{ik} = \begin{cases} 1 & \text{if task } i \text{ starts at unit } k. \\ 0, & \text{otherwise.} \end{cases}$$

Multiple input variables can be defined to be able to encapsulate medical provider specific requirements. The binary input variable $e_{ijk}$ can be used to identify staff that can work at time unit k, i.e., available, and task i lists staff j as eligible:

$$e_{ijk} = \begin{cases} 1 & \text{if medical provider } j \text{ is available and eligible to perform task } i \text{ at time unit } k. \\ 0, & \text{otherwise.} \end{cases}$$

This variable can be used to prevent assignments that are not feasible in terms of staff availability or certification or expertise. A target task amount can be associated to each personnel denoted as $t_{j,target}$ and a staffing cost per unit time slot for task i and staff j as $c_{ij}$.

The scheduling system can then use the information provided by the score calibrator, in the embodiments where present, in scheduling the tasks. In particular, each task can be associated with a score vector, $sv_i$ that distributes the risk of the patient with respect to underlying conditions. For the purposes of scheduling, this score vector can be mapped to a scalar value using a function $f: \mathcal{R}^N \to \mathcal{R}^+$, that accepts the N-dimensional score vector as input. The choice for the function $f$ an differ based on the preferences of the hospital or the unit. Example choices include, but are not limited to, weighted averaging, mean, median and maximum of the score vector $sv_i$. The scalar urgency value of the task can be then denoted by $u_i$ such that $f(sv_i)=u_i$.

The optimization and input variables described above can thus be listed as in the table below:

| Variable Name | Definition | Type |
| --- | --- | --- |
| $x_{ijk}$ | 1 if task i is assigned to staff j at time unit k | Optimization |
| $d_i$ | Duration of task i in terms of time bins | Input |
| $w_i$ | The duration task i has been in the task pool | Input |
| $y_{ik}$ | 1 if task i starts at time unit k | Optimization |
| $e_{ijk}$ | 1 if staff j is eligible to perform task i at time unit k | Input |
| $c_{ij}$ | Cost of task i, being performed by staff j | Input |
| $t_{j, target}$ | The target task amount staff j has to | Input |
| $sv_i$ | Score vector of task i due to the score coordinator | Input |
| $u_i$ | Urgency value of task i | Input |

The constraints for scheduling system can then be summarized as follows:

Completion of tasks with respect to availability and eligibility: each task is preferably completed with respect to availability and eligibility constraints:

$$\sum_{j \in \mathcal{J}} \sum_{k \in \mathcal{K}} x_{ijk} e_{ijk} = d_i, \forall i \in \mathcal{T}.$$

Completion of the task by single personnel: to formulate this constraint an indicator function $\mathcal{I}: Z_+^{N \times J} \to \{0,1\}^{N \times J}$ can be defined. Here $Z_+$ can refer to the set of all non-negative integers. The constraint can then be written as:

$$\sum_{j \in P} \mathcal{I}\left\{\sum_{k \in \mathcal{K}} x_{ijk}\right\} = 1, \forall i \in T$$

Continuity of each task: These constraints incorporate the start time of the task and ensure that once a task is started, it can end without interruption:

$$\sum_{j \in \mathcal{J}} x_{ijk} = \sum_{l=max(1,k-d_i+1)}^{k} y_{il} \forall i \in T, \text{ and } \forall k \in \mathcal{K}$$

This allows that if $x_{ijk}=1$ then $y_{ik}$ has to be 1 within the duration of the task as it must have started. The following constraint ensures that tasks finish without interruption:

$$\sum_{l=1}^{k_{max}-d_i+1} y_{il} = 1, \forall i \in \mathcal{T}.$$

Maximum wait time for a task: to prevent a task being on the task fool for an indefinite amount of time, the following constraint can be incorporated:

$$w_i + \sum_{l \in \mathcal{K}} y_{il} \times l \leq \text{max\_wait\_time}, \forall i \in \mathcal{T}$$

In this constraint any wait time that might have been accumulated before the current scheduling effort can be accounted for, via the inclusion of $w_i$. Here the variable max_wait_time can be a user defined input that sets a time limit on the maximum time a task can stay in the job pool.

In some embodiments, a modified version of this constraint can be used to avoid infeasibilities in cases where it is not possible to schedule a task due to lack of eligible medical staff or other availability issues. The constraint can then be modified to include the non-negative slack variable lat $e_i$ for each task i:

$$w_i + \sum_{l \in \mathcal{K}} y_{il} \times l \leq \text{max\_wait\_time} + late_i, \forall i \in \mathcal{T}$$

In order to avoid unnecessary delays, the slack variables, $late_i$, can be incorporated into the objectives that will be explained below.

Deviation from target task amount: a target amount of task each medical staff should perform in the scheduling period is denoted by $t_{j,target}$. Since it might not be possible to exactly match the target value, due to excess demand or lack of demand or urgencies, two non-negative slack variables, $t_{j,over}$ and $t_{j,under}$, can be used to compensate for the deviation from the target:

$$\sum_{i \in \mathcal{T}} \sum_{k \in \mathcal{K}} d_i \times x_{ijk} - t_{j,over} + t_{j,under} = t_{i,target}, \forall j \in \mathcal{P}$$

When a staff gets assigned more tasks than they are supposed to then $t_{j,over}>0$ and $t_{j,under}=0$. When a staff gets assigned less tasks than they are supposed to then $t_{j,over}=0$ and $t_{j,under}>0$.

The scheduling system can then optimize for any of the following objectives:

Minimization of late tasks: this objective is directly related to Constraint 4 where slack variables are used to bend the maximum wait time in the task pool:

$$O_{late} = \sum_{i \in \mathcal{T}} g_i(late_i),$$

where $g_i(.)$ is a function through which the slack variables are mapped to costs. In linear optimization this function is usually chosen as the identity mapping. Alternatively, or in addition, quadratic, piece-wise linear or other functions can be chosen to more heavily penalize large values of $late_i$.

Minimization of urgency-weighted turn-around-time: this objective uses the urgency score of the tasks, $u_i$, to minimize the turn around time of the jobs:

$$O_{TAT} = \sum_{i \in \mathcal{T}} h_i\left(\sum_{l \in \mathcal{K}} y_{il} \times l, u_i\right),$$

where the term $\sum_{l \in \mathcal{K}} y_{il} \times l$ identifies the start time of the task and the function $h_i(.)$ combines the start time with the urgency of task and maps to it a cost value.

One possible choice for this function can be the multiplicative weighting of the start time with the urgency value such as $h_i(\sum_{l \in \mathcal{K}} y_{il} \times l, u_i) = u_i \times (\sum_{l \in \mathcal{K}} y_{il} \times l)$. Alternatively, or in addition, other functions such as quadratic forms that penalize the weighted start time more aggressively can be used.

Task-Staff Correlation: this objective function seeks to maximize the correlation of the task and staff assignments. Each task can be represented by a few keywords stemming from such as the type of exam, anatomy, suspected findings, and its translation into a real-valued vector denoted by $td_i$. Similarly, each medical personnel can be associated with a profile that summarizes their expertise denoted by $pd_j$. Then the cost function becomes:

$$O_{corr} = \sum_{i \in \mathcal{T}} \sum_{j \in \mathcal{P}} v(td_i, pd_j) \mathcal{I}\left(\sum_{k \in \mathcal{K}} x_{ijk}\right),$$

where $v(.)$ is a measure of correlation and or fit and the inner most summation with the indicator function is used to count each task once even though they can span multiple time bins.

Minimize operational cost: through this objective, the assignment costs can be minimized:

$$O_{cost} = \sum_{i \in \mathcal{T}} \sum_{j \in P} \sum_{k \in \mathcal{K}} c_{ij} \times d_i \times x_{ijk}$$

Load Balancing Across Medical Staff: this objective is related to constraint 5. The slack variables defined in that constraint are used in this objective to minimize the deviation from the target task amounts:

$$O_{LB} = \gamma_j \sum_{j \in \mathcal{P}} n_{j,over}(t_{j,over}) + \eta_j \sum_{j \in \mathcal{P}} n_{j,under}(t_{j,under}).$$

Here $n_{j,over}(.)$ and $nj_{,under}(.)$ can be functions that penalize the slack variables. Various functions can be implemented, such as any of linear functions, non-linear and piecewise linear functions, to achieve balanced distribution of task amounts. $\gamma_j$ and $\eta_j$ can be used to individually weigh each cost term.

The scheduling system can thus have up to five cost functions that aim at optimizing different aspects of task assignment and scheduling. The user, such as a healthcare provider, can prioritize between these objectives. If an ordering of the objectives in terms priority exists, this can be translated to lexicographic optimization. A weighting of the objects can be used as well. Here an example is provided with five objectives:

$$O_{total} = b_1 O_{late} + b_2 O_{TAT} + b_3 O_{corr} + b_4 O_{cost} + b_5 O_{LB},$$

where $b_1, b_2, b_3, b_4, b_5 \in \mathcal{R}^+$. The scheduling system defined above can thus be seen as a mixed integer optimization.

Although various constraints and objectives have been disclosed, other constraints and objectives can be easily added to the scheduling system to encapsulate the needs of the healthcare providers. Similarly, constraints and objectives can be removed if they are deemed unnecessary.

The scheduling system can thus be used to optimize the task assignments each time a new task is added to the task pool by keeping the existing assignments for uncompleted tasks and updating the wait times for each task accordingly.

Although various embodiments of the invention have been described above with reference to specific characteristics for each embodiment, the present invention is not limited to the embodiments described. In particular, additional embodiments falling within the scope of the invention can be implemented by combining one or more of the features of a given embodiment with one or more of the features of one or more of the remaining embodiments.

Moreover, the various methods described above can be implemented by a computer program or a computer-program product or a computer-readable storage medium including program code. The program code can be loaded and executed by at least one processor. Upon loading and executing the program code, the at least one processor can perform a scheduling method for processing of medical data in accordance with any of the methods described above.

The invention claimed is:

1. A scheduling system comprising:
   a plurality of input devices configured to output medical data for a plurality of different patients,
   a workforce storage configured to store working characteristics of a plurality of doctors,
   a plurality of data analysers configured to receive the medical data, analyse the medical data so as to assign a score indicative of urgency of the medical data, and output a scored medical data,
   a score calibrator configured to receive the scored medical data, analyse the scored medical data so as to calibrate the score of the medical data, and output calibrated medical data, and
   a scheduler configured to construct a plurality of schedules for analysis of the medical data by the plurality of doctors, wherein the plurality of schedules according to which the plurality of doctors analyse the medical data is constructed based on characteristics of the calibrated medical data and the working characteristics of the plurality of doctors.

2. The scheduling system of claim 1, wherein analysis of the medical data is continuously optimized based on incoming medical data.

3. The scheduling system of claim 1, wherein the scheduler is configured so as to construct the plurality of schedules so as to maximize a correspondence between a medical condition associated to the medical data and specialties of the plurality of doctors and minimize a turn-around-time for analysing the medical data in consideration of an urgency of various conditions associated with various pieces of the medical data.

4. The scheduling system of claim 1, further comprising a plurality of data analysers configured to receive the medical data from the plurality of input devices, analyse the medical data so as to assign a score indicative of urgency of the medical data, and output a scored medical data, and wherein the data related to the medical data is the scored medical data.

5. The scheduling system of claim 1, wherein the scored medical data comprises a plurality of pieces of scored medical data, any given piece of scored medical data comprising medical data and a risk score, wherein the score calibrator, for analysis of the scored medical data, is configured to:
  for a given piece of scored medical data, estimate prior probability as empirical probabilities reported in literature or measured from historical records,
  for the given piece of scored medical data, estimate conditional probabilities for relevant findings as a function of the risk score associated to the given piece of scored medical data,
  construct a graphical model of an interrelation between the plurality of risk scores and the plurality of findings, and
  infer a posterior probability of a clinical state associated to the given piece of medical data, preferably using Bayesian inference.

6. The scheduling system of claim 5,
  wherein the score calibrator, for the estimation of the conditional probabilities, is configured to estimate the conditional probabilities using documented performance measures and/or using classifier calibration techniques.

7. The scheduling system of claim 1, further comprising an objective storage configured to store one or more objectives for the operation of the scheduler, wherein the scheduler is further configured to receive as input the one or more objectives.

8. The scheduling system of claim 1, further comprising a constraints storage configured to store one or more constraints, wherein the scheduler is further configured to receive as input the one or more constraints.

9. The scheduling system of claim 1, wherein the medical data comprises any of radiology image, in vitro data, and recorded patient data.

10. A scheduling method comprising:
  receiving medical data output by a plurality of input devices,
  assigning a score indicative of urgency of the medical data,
  outputting a scored medical data,
  receiving the scored medical data,
  calibrating the score of the scored medical data,
  outputting a calibrated medical data,
  receiving as input the calibrated medical data and working characteristics of a plurality of doctors, and
  constructing as output a plurality of schedules for analysis of the medical data by the plurality of doctors, wherein the plurality of schedules are constructed based on the calibrated medical data and working characteristics.

11. The method of claim 10, wherein the medical data is continuously optimized based on incoming medical data.

12. The method of claim 10, wherein constructing comprises:
  constructing the plurality of schedules so as to maximize a correspondence between a medical condition associated to the medical data and specialties of the plurality of doctors and minimize a turn-around-time for analysing the medical data in consideration of an urgency of various conditions associated with various pieces of the medical data.

13. The method of claim 10, wherein the scored medical data comprises a plurality of pieces of scored medical data, any given piece of scored medical data comprising the medical data and a risk score, wherein, analysing the scored medical data comprises:
  for a given piece of scored medical data, estimating prior probability as empirical probabilities reported in literature or measured from historical records,
  for the given piece of scored medical data, estimating conditional probabilities for relevant findings as a function of the risk score associated to the given piece of scored medical data,
  constructing a graphical model of an interrelation between the plurality of risk scores and the plurality of findings, and
  inferring a posterior probability of a clinical state associated to the given piece of medical data, preferably using Bayesian inference.

14. The method of claim 13, wherein estimating the conditional probabilities comprises estimating the conditional probabilities using documented performance measures and/or using classifier calibration techniques.

15. The method of claim 10, further comprising:
  storing one or more objectives for the operation of a scheduler,
  receiving as input the one or more objectives.

16. The method of claim 10, further comprising:
  storing one or more constraints,
  receiving as input the one or more constraints.

17. The method of claim 10, wherein the medical data comprises any of radiology image, in vitro data, and recorded patient data.

* * * * *